(12) United States Patent
Bennardo

(10) Patent No.: US 6,206,889 B1
(45) Date of Patent: Mar. 27, 2001

(54) DEVICE FOR REMOVING ANATOMICAL PARTS BY LAPAROSCOPY

(76) Inventor: Roberto Bennardo, Via B. Latini 20, 20026 Novate Milanese (IT)

(*) Notice: Subject to any disclaimer, the term of this patent is extended or adjusted under 35 U.S.C. 154(b) by 0 days.

(21) Appl. No.: 09/254,042
(22) PCT Filed: Jun. 26, 1998
(86) PCT No.: PCT/EP98/04034
§ 371 Date: May 25, 1999
§ 102(e) Date: May 25, 1999
(87) PCT Pub. No.: WO99/01068
PCT Pub. Date: Jan. 14, 1999
(51) Int. Cl.⁷ ............................................. A61B 17/22
(52) U.S. Cl. ............................ 606/127; 128/DIG. 24; 600/562
(58) Field of Search .................... 606/114, 127, 606/1, 562; 128/DIG. 24

(56) References Cited

U.S. PATENT DOCUMENTS

| | | |
|---|---|---|
| 3,108,593 * 10/1963 | Glassman | 606/127 |
| 5,147,371    9/1992 | Washington et al. . | |
| 5,312,416 *  5/1994 | Spaeth et al. | 600/562 X |
| 5,341,815    8/1994 | Cofone et al. . | |
| 5,354,303 * 10/1994 | Spaeth et al. | 606/114 X |
| 5,480,404    1/1996 | Kammerer et al. . | |
| 5,769,794 *  6/1998 | Conlan et al. | 600/562 |

* cited by examiner

*Primary Examiner*—Jeffrey A. Smith
(74) *Attorney, Agent, or Firm*—Pillsbury Madison & Sutro LLP

(57) ABSTRACT

A device for the removal of anatomical parts by laparoscopy, comprising a bag to be inserted by means of a tube applicator inside the abdominal cavity. A flexible element is provided along the edge of the mouth of the bag, having such resilient characteristics as to spring back to a loop configuration when it is not subjected to a deformation. According to a preferred embodiment, the flexible element is formed by a helicoidal spring with a ring clip slidingly coupled thereto, so that the resilient action of the spring keeps the mouth open when the bag is inserted in the abdominal cavity, and by making the clip to slide along the spring it is possible to close again the bag when needed.

9 Claims, 3 Drawing Sheets

DEVICE FOR REMOVING ANATOMICAL PARTS BY LAPAROSCOPY

This application is the national phase of international application PCT/EP98/04034 filed Jun. 26, 1998 which designated the U.S.

FIELD OF THE INVENTION

The present invention relates to a device for removing anatomical parts, devised for surgical operations carried out by laparoscopy.

In a most specific manner, this device comprises a bag wherein the aforesaid parts are placed back and a tube applicator wherein the bag is arranged for being introduced in an abdominal cavity to be operated; the applicator is also provided with means for ejecting the bag out into the cavity above.

DESCRIPTION OF THE RELATED ART

The surgical operations previously referred to, have been studied and developed in recent time; they allow to operate inside the abdominal cavity of a patient, avoiding to make the wide incisions that usually mark the traditional surgical operations: examples of treatments that actually are carried out with laparoscopic technique are the taking of samples of tissues like the appendix or cholecystes, the extirpation of calculi and cyst, as well as some gynecological treatments.

In practice the operations herein considered consist of making on the patient's abdomen some apertures or laparatomies, usually at least two and no more than four, having diameter of few millimeters (from 5 to 15 mm) and devised for the insertion into the abdominal cavity of surgical instruments suitably adapted to this purpose; these instruments may be optical waveguide probes, scissors, pliers, suture devices or, like in the case of the present invention, devices for removing anatomical parts to be taken or extirpated.

Actually two models of the device just mentioned, are known in commerce. The first one, generally considered as the best by the persons of the art even though more expensive, comprises a polyurethane bag on the mouth thereof there is applied a pretensioning metallic ring, resiliently folding and having a diameter of 10 or 15 cm depending on the models; the polyurethane bag is also provided with a twisted polyamide seam, that allows its tightening like a tobacco bag thereby separating it in an automatic manner from the pretensioning ring, by means of a cutting edge of the latter.

The ring in an initial folded condition, together with the empty bag, is located in a cylindrical tube of 10 or 15 mm of diameter, which is inserted into the abdominal cavity to be operated through one of the laparatomies already referred to.

The use of the known device just considered takes place according to a sequence of steps as follows.

After having inserted a distal end of the cylindrical tube into the abdominal cavity of the patient, the bag is pushed out in said cavity by a cursor acting on it, similar to that of a normal syringe and operated from the proximal end of the tube: in this situation the pretensioning ring may thus unfold close to the area to be surgically operated by virtue of its spring action, thereby promptly disposing the related bag in an open condition, ready to accomodate an anatomical part to be removed.

After the part has been put into the bag, the latter is closed by narrowing its mouth pulling the aforesaid polyamide seam; following to this phase the bag is cut off the pretentioning ring and the latter, after having been previously folded, may be drawn out from the cylindrical tube while the former is pulled toward the distal and of the tube: afterward, also the bag may be slipped out of the cavity together with the tube.

On this subject it is pointed out that for the known model of device just described, it is also foreseen the possibility of keeping the bag open inside the abdominal cavity after the pretensioning ring has been drawn out: in this case, however, the detachment of the ring from the bag must be made differently from what has been said before, that is not by closing the mouth of the bag following to the pulling of its polyamide seam, but rather by acting inside the abdominal cavity for making a partial cut of the bag in correspondence of the ring.

From what has been stated heretofore, it is possible to understand that although this known device has the advantage of an automatic and quick opening of the bag thanks to the resilient pretensioning ring, it is however marked by a scarce handyness because of the dimensions of the ring once the latter is open inside the cavity to be operated, and of a certain functioning labouriousness; above all it must be underlined the fact that in this known device, once the bag is closed it is no more possible to re-open it: in other words, with such a device it is not possible to carry out cycles of opening and subsequent closing of the bag which are useful in some kinds of operations, such as those wherein several anatomical parts must be removed (extirpations of small lymph nodes, multiple biopsies) in sequence inside the abdominal cavity, without the risk of their dispersion.

As an alternative to the removing device discussed heretofore, there exists another one available in commerce.

The latter device is provided with the usual bag wherein the anatomical parts are accommodated, whose mouth is however coupled with a flexible ribbon made of plastics such as NYLON (registered trademark) or the like; the bag is applied on the distal end of a cannula and for this reason it is provided with an appendix in correspondence of its mouth, to be sealed on such an end.

The above mentioned ribbon is located for a portion in a turn-up edge of the mouth of the bag, whereas its two free ends are arranged inside the above mentioned cannula and are connected to the tip of a cursor rod axially slidable within it: in this manner the ribbon takes a loop configuration that will be better appreciated later. Likewise the previous model, in this device the cursor is operated from the proximal end of the cannula like a syringe and moves between a forward end stroke position and a rearward one.

In accordance with the movements of the cursor, the ends of the ribbon connected to it are placed, respectively, adjacent to the distal end of the cannula or inside to it: in the first case the ribbon protrudes basically for all its length off the distal end of the cannula and the loop that it forms has such a length as to allow the mouth of the bag to be in the maximum opening condition; in the second case, instead, the ribbon is located mainly inside the cannula so that the mouth of the bag is closed following to the relative sliding between its turned-up edge and the ribbon.

This second model of device just referred to allows, differently from the first one, to carry out repeated opening and closing cycles of the bag, thereby representing under this point a technical improvement; this outcome is due essentially to the fact that it does not have a rigid pretensioning ring associated to the mouth of the bag, but rather a flexible element like the ribbon made of plastic material.

However it is not able to ensure an automatic and quick first opening of the bag like it occurs for the previous example.

It must indeed been taken into account that when the distal end of the cannula is introduced in the abdominal cavity, for opening the bag applied thereto the surgeon must make use of pliers or other surgical instruments because even by acting on the cursor of the device, the ribbon surrounding the mouth of the bag cannot lay itself in the loop configuration sought: this is due to the intrinsic features of the ribbon useful for folding it as explained before. Similar difficulties may further arise also in the case of possible subsequent opening phases of the bag, thereby limiting infact the performances of this device. It can also be appreciated that the limit just outlined relating to the opening of the bag, increases with the growth of the dimensions: it can indeed be understood that the difficulties for unfolding the material of the bag are increased by such a growth, in particular for what it concerns the mouth and the capability to achieve the loop configuration of the ribbon. This argument may thus explain the reason why this second known model of device is available in commerce with bags of small dimensions, which are therefore not useful for removing anatomical parts of a certain size.

SUMMARY OF THE INVENTION

The object that the present invention purposes to achieve is that of providing a device for removing anatomical parts, having such structural and functional features as to overcome the limits concerning the devices of the state of the art and that have been previously explained.

In other terms it can be said that the invention is aimed at providing a removing device wherein the first opening of the bag inside the abdominal cavity takes place in a quick and autonomous manner, i.e. without the intervention of the surgeon to unfold the material of the bag and to open the mouth thereof likewise it occurs in the first model above, as well as wherein the closing and opening for several times of the bag is possible.

This object is achieved by a device for removing anatomical parts of the type referred to above, characterized in the claims annexed to this description.

BRIEF DESCRIPTION OF THE DRAWINGS

For better understanding the invention as a whole, with its features and the advantageous effects resulting therefrom, it is now put forward a detailed description of two preferred and non-exclusive embodiments, shown in the attached drawings wherein.

Figure 1:
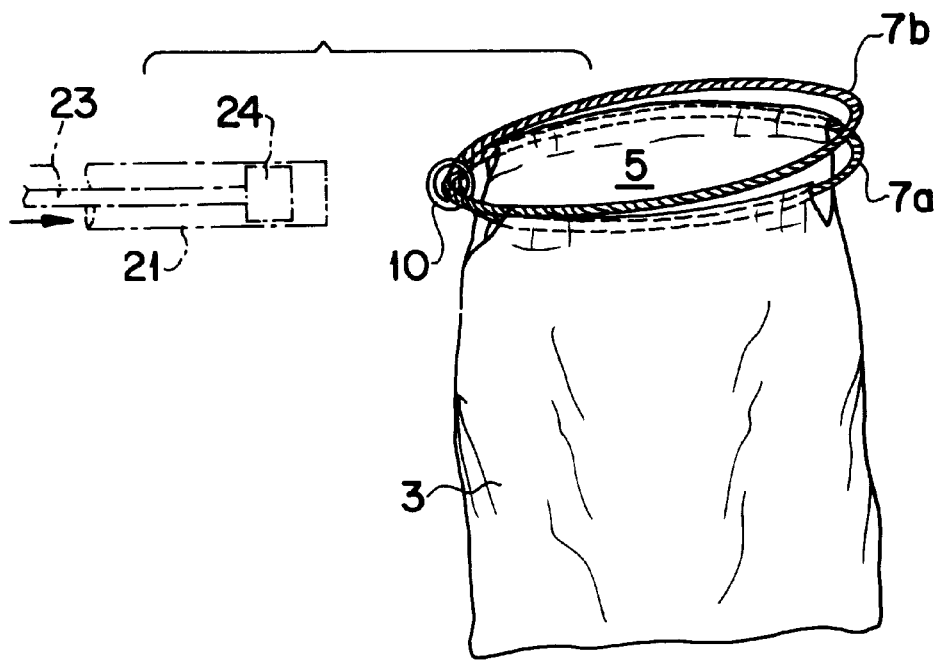
FIGS. 1 and 2 show a perspective view of an open bag relating to first example of device according to the invention, in respective subsequent operating conditions.

Considering first the FIGS. 1–5, they show a device according to this invention generally indicated as 1.

DETAILED DESCRIPTION OF THE DRAWINGS

The device includes a bag 3, made preferably of plastic resistant material such as polyurethane, KEVLAR (registered trademark) for high strength aramid fiber or polypropylene, having a mouth 5 wherein a flexible element 7 is arranged; the latter advantageously consists of a helicoidal closed spring, that is to say without free ends, of the type similar to a wire, having such a resilient behaviour as to spring back in a loop configuration when it is not subjected to a deformation.

More specifically, the flexible element 7 is folded like an "8" and a ring 10 arranged astride the two lobes that form this "8" (best seen in FIG. 2), is provided as a clip for ensuring the stability of the folding: a first lobe 7a formed by flexible element 7, is arranged within a flap 11 extending along the edge of the mouth 5 of the bag 3, whilst the second lobe 7b is free.

The portions of the lobes 7a and 7b are not fixed as will better result in the continuation of this description, but may vary by making the ring 10 to slide along the flexible element 7: for this reason the ring exhibits a certain clearance in its coupling with the flexible element.

In the device 1 of this invention there is also an applicator basically consisting of a cylindrical tube 21, having a distal end 21a open for pennitting the ejection of the bag 3 as it will better result later, and a proximal end 21b closed by a base 22 in sealing relationship with a stem 23 axially slidable back and forth; on the tip of the stem which is located inside the tube, there is a small ram 24, whilst the seal on the stem is provided by an annular ship membrane 25, arranged transversely the tube and around the stem.

Finally, to allow the handling of the applicator by the surgeon in a manner similar to a syringe, the tube 21 is also provided with two wings 26 in connection with its proximal end 21b.

The various parts of the device according to the present invention that have been described up to now separated from each other, are assembled for the functioning of the device as follows.

Figure 3:
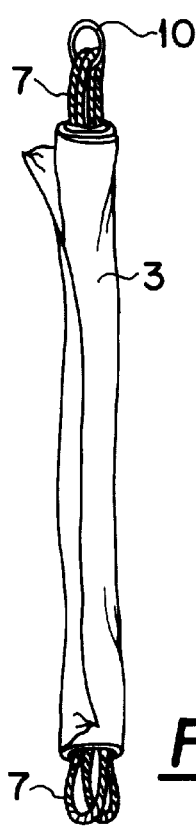
FIG. 3 shows a detailed view of the aforesaid bag, in the rolled up condition suitable for being introduced into an abdominal cavity.

The flexible element 7 associated to the bag 3 is first folded so as to overlap the two lobes of the "8" profile previously referred to, as shown in FIG. 1; afterwards the bag is wrapped around the flexible element so as to take the tubular form shown in FIG. 3: it is worth to consider that in this condition the flexible element, which consists of a spring, is deformed an thus exerts a resilient reaction giving rise to the effects that will be dealt with later. It is also to be stressed in connection with FIGS. 3 and 4, that in this phase the ring 10 is located outside the wrapped bag.

Figure 4:
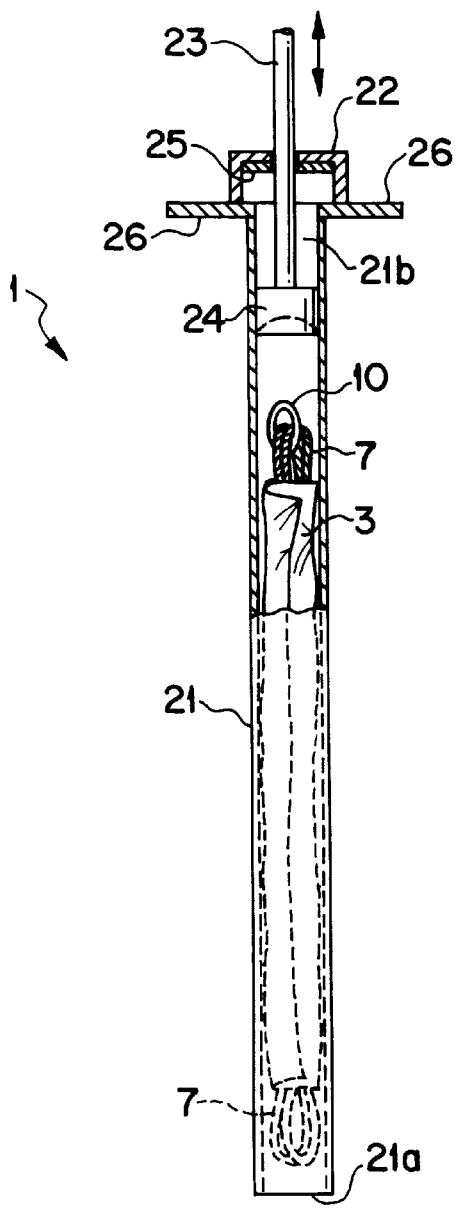
FIG. 4 shows a partially sectional view with a cut away portion, of the first embodiment above mentioned of device according to the invention.
Figure 5:
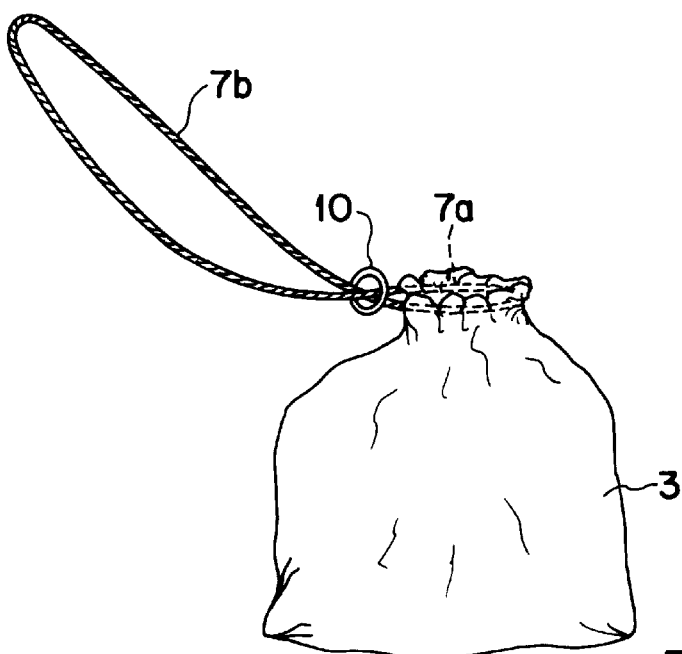
FIG. 5 shows the bag of the preceding figures, in a condition wherein its mouth is closed.

The latter is then inserted into the tube 21 of the applicator and the device thereby finished is shown in FIG. 4: it matters to observe that in this condition the device can be easily packed, ready for use, in sterilized packagings like sealed envelopes or whatever else, thereby resulting quite advantageous under this aspect.

For using the device of this invention starting from the condition of FIG. 4, the distal end 21a of the tube is inserted into the abdominal cavity to be operated through a laparatomy, in the desired position; pushing the stem 23 in the tube 21, the ram 24 solid therewith moves forward the distal end 21a and acts on the bag thereby ejecting it out of the tube.

Once this phase is ended, the bag becomes free to unroll; this takes place in an autonomous manner, within the meaning of this term already explained: indeed thanks to its resilience, the helicoidal spring constituting the flexible element 7 springs back into the "8" configuration already referred to and the elastic reaction that it exerts for assuming this configuration, allows to unroll the bag wrapped around it. It goes without saying that the resilience of the spring must be suitably chosen in order to achieve the effect just pointed out, for instance by taking into account the dimensions of the different parts that form the device, as well as the type of bag used and whatever else.

Figure 2:
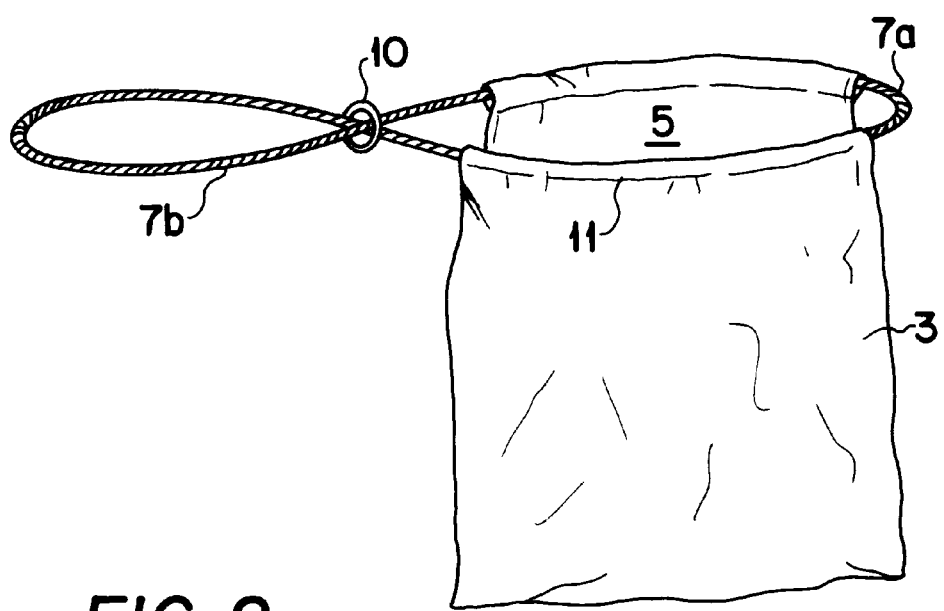

The bag 3 will thus dispose with its mouth open in the condition shown in FIG. 2, while the flexible element 7 assumes the "8" configuration: from this moment any surgical operation inside the cavity can be carried out, since it is possible to handle the bag with the greatest simplicity because the lobe 7b of the flexible element may be used as a gripping point for surgical pliers, while the bag is kept open by the resilient action of the spring forming the flexible element.

For closing the bag after use, the lobe 7b is pulled holding the ring 10 still (see FIG. 5): the latter, indeed, in this manner has in practice the function of a noose and following to the pull, the proportions of the lobes 7a and 7b change so that the former narrows whereas the latter widens; the edge of the mouth 5 of the bag is therefore narrowed too in this connection, thereby obtaining the desired closing.

Likewise, for opening again the bag starting from this condition it is sufficient to operate in the reverse manner by making the ring 10 to slide with respect to the flexible element 7, thereby bringing the two lobes 7a and 7b back to the initial dimension which in this case correspond to what is shown in FIG. 2; it must be underlined that the flexible element 7 also helps to take the bag back to the open condition by means of its resilience, and it aspect makes it possible to carry out repeated closing and opening cycles of the bag without any difficulties.

From what has been said heretofore it can thus be appreciated that the device according to the invention achieves the object set out initially.

Indeed it has been shown that for what it concerns the first opening of the bag inside the abdominal cavity, it takes places in a quick manner and without the need for a specific intervention of the surgeon for unrolling the bag, likewise in the first known model of device previously considered; furthermore, the device according to the present invention allows to open and close many times the bag in order to put therein the anatomical parts subsequently removed, thanks to the resilient behaviour of the flexible element explained in connection with the embodiment described.

In other words it can be said that in the device of the invention, the flexible element 7 gives the same performances of the already cited pretensioning ring of the state of the art, as regards the first opening of the bag: however, thanks to its flexibility and resilience, such element may be deformed repeatedly in order to allow the cyclic closing and opening of the bag.

A further important effect related to the present invention resides in the fact that also from a medical point of view, it does not involve contraindications; more specifically, from the foregoing it may be appreciated that the use of the flexible element does not bring risks of lesions inside the abdominal cavity wherein the device is applied: indeed, even if such element during the opening of the bag hit the wall of the cavity or of any organ contained therein, its flexibility avoid damages to the tissues against which it comes into contact, thereby preventing the danger of injuries. It is also evident that such an advantageous effect is important when account is taken of the authorisations which must generally be obtained for put into commerce this kind of devices.

Moreover it has to be underlined that the outcomes of the invention explained heretofore, cannot be achieved by the device of the second known model considered before; indeed, the ribbon thereof made from plastic material, is only flexible but does not provide a resilient action comparable at all with the one of the flexible element according to this invention: consequently in such a known device the first opening of the bag is affected by the same problems already discussed above and in addition, also the subsequent opening and closing phases are conditioned by the defects arising from the intrinsic functioning features previously pointed out.

Figure 6:
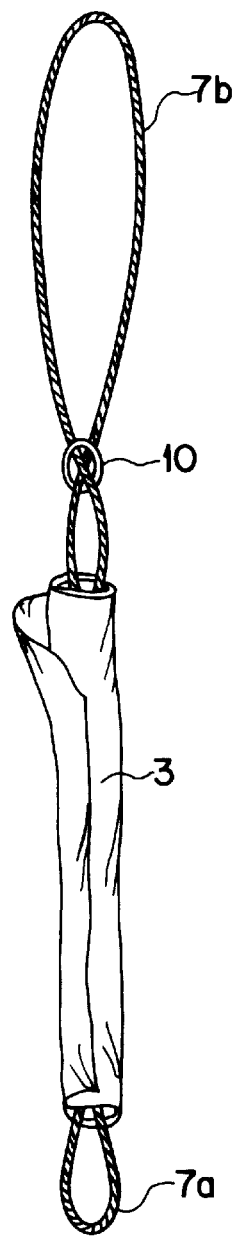
FIG. 6 shows in detail the bag according to a second embodiment of the invention, in the rolled up condition suitable for being introduced in a abdominal cavity.
Figure 7:
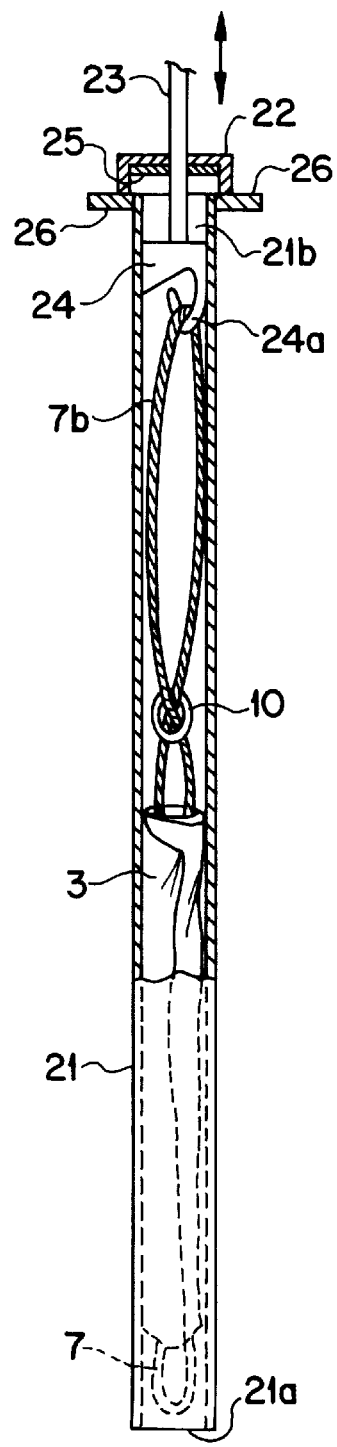
FIG. 7 shows a partially sectional view with a cut away portion, of the second embodiment of device according to the invention.

For seek of completeness in this description, there will now be given some short explanatory notes about the second embodiment of the invention shown in FIGS. 6 and 7, wherein the features structurally or functionally equivalent to those already considered in the first one, are indicated by the same numbering. In short, this second embodiment differs from the preceding one in that the bag 3 is wrapped for being inserted into the tube 21 of the applicator (see FIG. 6), only around the lobe 7a of the flexible element 7 associated to the edge of the mouth of the bag; in this manner, by providing the ram 24 with a hook portion 24a, the lobe 7b which is located outside the rolled bag, may be secured to that portion thereby allowing to retrieve the bag 3 after the surgical operation: indeed it just needs to withdraw the stem 23 into the tube 21, for bringing the bag 3 hooked to the ram 24 close to the distal end 21 of the tube and, should the dimensions of the anatomical piece(s) allow it, also into the tube itself. In so far the manner of carrying out the first opening of the bag for this embodiment is concerned, as well as the following repeated phases of opening and closing it, they take place in the same way explained above in connection with the first embodiment and therefore reference should be made on this point, to the corresponding part of the description.

Obviously further changes to the devices of the invention should not be excluded.

For instance it is suggested that the ring 10 be replaced by a buckle, a clamp or any other suitable fastener, which might also be adjustable so as to better slide along the flexible element: indeed it should be appreciated that although the ring above is an easy manufacturing element in industry and thus with low costs, it could also be improved giving rise to several alternative solutions. It must be further emphasised that the arrangement of the ring astride the junction of the two lobes 7a and 7b (see FIG. 2), allows to firmly keep the flexible element in the "8" configuration, preventing in the meantime the ring from slipping off it: in other terms, as a possible alternative embodiment it could be thought to arrange the ring like a belt fastened around the junction, but this would seemingly involve the possibility of its slipping off the flexible element 7 during use of the device, with all the connected risks that may be easily imagined.

As a further change with the respect to what has been described heretofore, it might also be considered to eliminate the ring itself: indeed, although it is particularly advantageous for carrying out easily and effectively the closing and, should it be needed, the re-opening of the bag, these operations might however be carried out, although with more difficulties, thanks to the resilient spring back of the helicoidal spring forming the flexible element.

At last, also as regards the latter element other solutions cannot be excluded with respect to the helicoidal spring of the proposed embodiments; the spring indeed is particularly suitable for this invention because further to achieving the outcomes already explained, it has shown to be economically advantageous being available with low costs: however it must not be ruled out the possibility of using in place of it, metallic wires, elastomers or other flexible elements purposely produced according to the teaching of this invention.

All these and further possible embodiments fall however within this scope defined by the following claims.

What is claimed is:

1. A device for removing anatomical parts in surgical operations carried out by laparoscopy, comprising a bag, a tube applicator in which the bag is arranged for being introduced in an abdominal cavity, means for ejecting the bag from the tube applicator into said cavity, a flexible closed linear element associated with the bag along its mouth, having an elastic behavior so as to spring back in a loop configuration when the bag is outside the tube applicator, wherein the flexible element is slidingly coupled with a ring-shape clip which defines two lobes having substantially loop forms of variable dimensions following the reciprocal sliding between the flexible element and the clip.

2. A device according to claim 1, wherein the flexible element is a helicoidal spring.

3. A device according to claim 1, wherein the flexible element is folded into a figure 8 profile and wherein the clip is arranged astride a junction of the two lobes forming said figure 8 profile.

4. A device according to claim 1, wherein the means of the tube applicator for ejecting the bag comprises a ram that slides longitudinally inside the tube applicator, operated by a stem passing through a proximal end of the tube applicator, and wherein the applicator is provided with means for making a seal on the stem.

5. A device according to claim 4, wherein the means for making the seal on the stem comprises a membrane.

6. A device according to claim 4, wherein the tube applicator further comprises means for hooking the flexible element.

7. A device according to claim 6, wherein the means for hooking the flexible element comprises a hook portion of the ram.

8. A device according to claim 1, wherein the bag is arranged inside the tube of the related applicator and is rolled around the flexible element or a part thereof.

9. A device according to claim 1, wherein the bag comprises a member selected from the group consisting of polyurethane, an aramid fiber and polypropylene.

* * * * *